US00PP35241P2

(12) United States Plant Patent
Koot

(10) Patent No.: US PP35,241 P2
(45) Date of Patent: Jul. 4, 2023

(54) ***LANTANA* PLANT NAMED 'DOLANHAGOL 23'**

(50) Latin Name: *Lantana camara*
Varietal Denomination: Dolanhagol 23

(71) Applicant: DUMMEN GROUP B.V., De Lier (NL)

(72) Inventor: Arjan Koot, Oeffelt (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 18/072,088

(22) Filed: Nov. 30, 2022

(51) Int. Cl.
*A01H 5/02* (2018.01)
*A01H 6/86* (2018.01)

(52) U.S. Cl.
USPC ..... Plt./227

(58) Field of Classification Search
USPC ..... Plt./226, 227
See application file for complete search history.

*Primary Examiner* — Karen M Redden
(74) *Attorney, Agent, or Firm* — C. Anne Whealy

(57) ABSTRACT

A new and distinct cultivar of *Lantana* plant named 'Dolanhagol 23', characterized by its compact, upright and mounding plant habit; moderately vigorous growth habit and moderate growth rate; freely branching growth habit; dense and bushy plant form; dark green-colored leaves; early and freely flowering habit; long flowering period; flowers that are dark yellow in color; and good garden performance.

1 Drawing Sheet

Botanical designation: *Lantana camara.*
Cultivar denomination: 'DOLANHAGOL 23'.

CROSS-REFERENCED TO CLOSELY-RELATED APPLICATIONS

Title: *Lantana* Plant Named 'DOLANHEARORA'
Inventor: Arjan Koot
Filed: Nov. 30, 2022; concurrently with the instant application.

An European Community Plant Breeder's Rights application for the instant plant was filed by the Applicant/Assignee, Dümmen Group B.V. of De Lier, The Netherlands on Aug. 5, 2022, application number 2022/1854. Foreign priority is not claimed to this application.

BACKGROUND OF THE INVENTION

The present invention relates to a new and distinct cultivar of *Lantana* plant, botanically known as *Lantana camara* and hereinafter referred to by the name 'Dolanhagol 23'.

The new *Lantana* plant is a product of a planned breeding program conducted by the Inventor in Rheinberg, Germany. The objective of the breeding program is to create new compact, freely-branching *Lantana* plants with early and freely flowering habit and large attractive flowers.

The new *Lantana* plant originated from a cross-pollination in July, 2019 in Rheinberg, Germany of a proprietary selection of *Lantana camara* identified as code number LA-0124, not patented, as the female, or seed, parent with a proprietary selection of *Lantana camara* identified as code number LA17-000101-001, not patented, as the male, or pollen, parent. The new *Lantana* plant was discovered and selected by the Inventor as a single flowering plant from within the progeny of the stated cross-pollination in a controlled greenhouse environment in Rheinberg, Germany in May, 2022.

Asexual reproduction of the new *Lantana* plant by terminal vegetative cuttings in a controlled greenhouse environment in Rheinberg, Germany since June, 2022 has shown that the unique features of this new *Lantana* plant are stable and reproduced true to type in successive generations.

SUMMARY OF THE INVENTION

Plants of the new *Lantana* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dolanhagol 23'. These characteristics in combination distinguish 'Dolanhagol 23' as a new and distinct *Lantana* plant:

1. Compact, upright and mounding plant habit.
2. Moderately vigorous growth habit and moderate growth rate.
3. Freely branching growth habit; dense and bushy plant form.
4. Dark green-colored leaves.
5. Early and freely flowering habit.
6. Long flowering period.
7. Flowers that are dark yellow in color.
8. Good garden performance.

Plants of the new *Lantana* can be compared to plants of the female parent selection. Plants of the new *Lantana* differ primarily from plants of the female parent selection in flower color as flowers of plants of the new *Lantana* are dark yellow in color whereas flowers of plants of the female parent selection are red and yellow in color. In addition, plants of the new *Lantana* have broader leaves than plants of the female parent selection.

Plants of the new *Lantana* can be compared to plants of the male parent selection. Plants of the new *Lantana* differ primarily from plants of the male parent selection in flower color as flowers of plants of the new *Lantana* are dark yellow in color whereas flowers of plants of the male parent selection are pink in color. In addition, plants of the new *Lantana* are not as compact as plants of the male parent selection.

Plants of the new *Lantana* can be compared to plants of the *Lantana camara* 'Dolanhearora', disclosed in a U.S. Plant patent application Ser. No. 18/072,108 filed concurrently. In side-by-side comparisons, plants of the new *Lantana* differ from plants of 'Dolanhearora' in the following characteristics:

1. Plants of the new *Lantana* are more compact than and not as vigorous as plants of 'Dolanhearora'.
2. Plants of the new *Lantana* have smaller inflorescences with smaller flowers than plants of 'Dolanhearora'.
3. Plants of the new *Lantana* and 'Dolanhearora' differ in flower color as flowers of plants of the new *Lantana* are dark yellow in color whereas flowers of plants of 'Dolanhearora' are initially orange in color becoming dark reddish orange with development.

Plants of the new *Lantana* can also be compared to plants of the *Lantana camara* 'Bamboo', not patented. In side-by-side comparisons, plants of the new *Lantana* differ from plants of 'Bamboo' in the following characteristics:

1. Plants of the new *Lantana* are more compact than and not as vigorous as plants of 'Bamboo'.
2. Plants of the new *Lantana* are more upright than and not as trailing as plants of 'Bamboo'.
3. Plants of the new *Lantana* have longer and broader leaves than plants of 'Bamboo'.
4. Plants of the new *Lantana* and 'Bamboo' differ in flower color as flowers of plants of the new *Lantana* are darker yellow in color than flowers of plants of 'Bamboo'.

BRIEF DESCRIPTION OF THE PHOTOGRAPH

The accompanying colored photograph illustrates the overall appearance of the new *Lantana* plant showing the colors as true as it is reasonably possible to obtain in colored reproductions of this type. Colors in the photograph may differ slightly from the color values cited in the detailed botanical description which accurately describe the colors of the new *Lantana* plant. The photograph is a side perspective view of a typical flowering plant of 'Dolanhagol 23' grown in a container.

DETAILED BOTANICAL DESCRIPTION

The aforementioned photograph and following observations and measurements describe plants grown during the spring and summer in 22-cm containers in a glass-covered greenhouse in Rheinberg, Germany and under commercial practices typical of commercial *Lantana* production. During the production of the plants, day and night temperatures averaged 18° C. and light levels ranged from 1,500 to 4,500 lux. Plants were pinched three weeks after planting and were twelve weeks old when the photograph was taken and 25 weeks old when the description was taken. In the following description, color references are made to The Royal Horticultural Society Colour Chart, Fifth Edition, except where general terms of ordinary dictionary significance are used.

Botanical classification: *Lantana camara* 'Dolanhagol 23'.

Parentage:

*Female, or seed, parent*.—Proprietary selection of *Lantana camara* identified as code number LA-0124, not patented.

*Male, or pollen, parent*.—Proprietary selection of *Lantana camara* identified as code number LA17-000101-001, not patented.

Propagation:

*Type*.—By vegetative terminal cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; close to 158A in color, actual color of the roots is dependent on substrate composition, water quality, fertilizers, substrate temperature and age of roots.

*Rooting habit*.—Freely branching; dense.

Plant description:

*Plant and growth habit*.—Compact, upright and mounding plant habit; moderately vigorous growth habit and moderate growth rate; freely branching habit, dense and bushy plant form.

*Plant height, soil level to top of foliar plante*.—About 21 cm.

*Plant height, soil level to top of floral plante*.—About 23.2 cm.

*Plant diameter*.—About 50 cm.

Lateral branch description:

*Branching habit*.—Freely branching habit with about six primary lateral branches each with about 16 secondary lateral branches developing per plant.

*Length*.—About 26 cm.

*Diameter*.—About 5.3 mm.

*Internode length*.—About 3.6 cm.

*Strength*.—Strong.

*Texture and luster*.—Pubescent; semi-glossy; longitudinally ridged.

*Color, developing stems*.—Close to 143A.

*Color, developed stems*.—Close to 165B.

Leaf description:

*Arrangement*.—Opposite, simple.

*Length*.—About 6.7 cm.

*Width*.—About 4.4 cm.

*Shape*.—Ovate.

*Apex*.—Acute.

*Base*.—Rounded.

*Margin*.—Serrate; sinuses are medium in depth and divergent.

*Texture and luster, upper surface*.—Coarse pubescence; semi-glossy.

*Texture and luster, lower surface*.—Coarse pubescence; matte.

*Venation pattern*.—Pinnate, reticulate.

*Color*.—Developing leaves, upper surface: Close to N137B. Developing leaves, lower surface: Close to 137C. Fully expanded leaves, upper surface: Close to N137A; venation, close to 138A. Fully expanded leaves, lower surface: Close to 137B; venation, close to 138B.

*Petioles*.—Length: About 1 cm. Diameter: About 1.5 mm. Strength: Moderately strong. Texture and luster: Smooth, glabrous; matte. Color, upper surface: Close to 137C. Color, lower surface: Close to 137D.

Flower description:

*Flower arrangement and flowering habit*.—Solitary salverform flowers arranged in terminal and axillary hemispherical umbels; flowers face mostly upward or outward depending on their position on the umbel; freely flowering habit with about 33 flowers per inflorescence and numerous inflorescences developing per plant during the flowering season.

*Natural flowering season*.—Early flowering habit, plants begin flowering about eight weeks from unrooted cuttings; long flowering period, plants of the new *Lantana* flower continuously from the spring into the autumn in Germany.

*Flower longevity on the plant*.—Individual flowers last about seven days; flowers persistent.

*Fragrance*.—None detected.

*Inflorescence height*.—About 4.5 cm.

*Inflorescence diameter*.—About 3.2 cm.

*Flower buds*.—Length: About 9 mm. Diameter: About 2.2 mm. Shape: Oval to tubular. Texture and luster: Rippled, glabrous; matte. Color: Close to 16A and 159C.

*Flowers*.—Appearance: Flared trumpet, salverform; corolla fused, five-parted. Diameter: About 8.3 mm by 7.4 mm. Depth (height): About 1.3 cm. Throat diameter: About 0.9 mm. Tube length: About 1 cm. Tube diameter: About 1.1 mm.

*Corolla*.—Arrangement: Single whorl of five fused petals. Petal lobe length: About 3 mm. Petal lobe width: About 3.5 mm. Petal lobe shape: Obovate. Petal lobe apex: Rounded. Petal margin: Entire; slightly undulate. Petal texture and luster, upper and lower surfaces: Smooth, glabrous; matte. Throat texture and luster: Smooth, glabrous; matte. Tube texture and luster: Smooth, glabrous; matte. Color: When opening and fully opened, upper surface: Close to 17B; venation, close to 17B; color does not change with subsequent development. When opening and fully opened, lower surface: Close to 17C; venation, close to 17C; color does not change with subsequent development. Throat: Close to 15B; venation, close to 15B. Tube: Close to 16C; venation, close to 16C.

*Calyx*.—Appearance: Tubular calyx with five fused sepals. Sepal length: About 6 mm. Sepal diameter: About 1.1 cm. Sepal shape: Ligulate. Sepal apex: Acute. Sepal margin: Entire. Sepal texture and luster, upper surface: Coarse pubescence; semi-glossy. Sepal texture and luster, lower surface: Coarse pubescence; matte. Sepal color, upper surface: Close to 137A. Sepal color, lower surface: Close to 137B.

*Peduncles*.—Length: About 2.8 cm. Diameter: About 1.2 mm. Strength: Strong. Aspect: Mostly upright. Texture and luster: Pubescent; semi-glossy. Color: Close to 149C.

*Pedicels*.—Length: About 1 mm. Diameter: About 1 mm. Strength: Strong. Aspect: Mostly upright. Texture and luster: Smooth, glabrous; semi-glossy. Color: Close to 144A.

*Reproductive organs*.—Stamens: Quantity and arrangement: Four per flower, adnate to floral tube. Anther length: About 0.6 mm. Anther shape: Oval. Anther color: Close to 17A. Pollen amount: Moderate. Pollen color: Close to 17C. Pistils: Quantity: One per flower. Pistil length: About 2.7 mm. Style length: About 1.1 mm. Style color: Close to 158B. Stigma diameter: About 0.2 mm. Stigma shape: Round. Stigma color: Close to 142A. Ovary color: Close to 140A. Fruits: Quantity produced per plant: About five during the flowering season. Length: About 5 mm. Diameter: About 7 mm. Texture: Rough. Color: Close to 202A. Seeds: Quantity per flower: About one to five. Length: About 4 mm. Diameter: About 5 mm. Texture: Smooth, glabrous. Color: Close to 200D.

Garden performance: Plants of the new *Lantana* have been observed to have good garden performance and to tolerate wind, rain and to be suitable for USDA Hardiness Zone 11.

Pathogen & pest tolerance: To date, plants of the new *Lantana* have not been observed to be tolerant to pathogens and pests common to *Lantana* plants.

It is claimed:

1. A new and distinct *Lantana* plant named 'Dolanhagol 23' as illustrated and described.

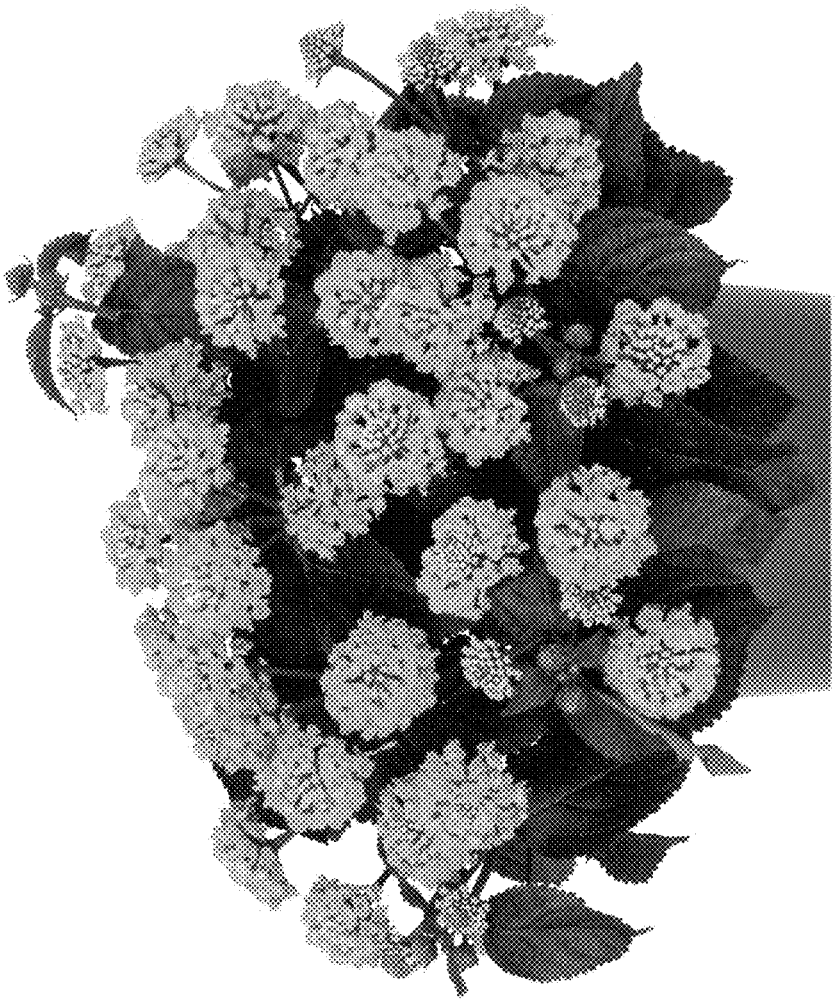

* * * * *